(12) United States Patent
Matos et al.

(10) Patent No.: US 8,889,403 B2
(45) Date of Patent: Nov. 18, 2014

(54) BIOREACTOR FOR ENGINEERED TISSUE

(75) Inventors: Marvi A. Matos, Seattle, WA (US);
William B. Carlson, Seattle, WA (US);
Ivan Vesely, Larkspur, CO (US);
Yansong Gu, Bellevue, WA (US)

(73) Assignee: Empire Technology Development LLC, Wilmington, DE (US)

(*) Notice: Subject to any disclaimer, the term of this patent is extended or adjusted under 35 U.S.C. 154(b) by 37 days.

(21) Appl. No.: 13/394,471

(22) PCT Filed: May 12, 2011

(86) PCT No.: PCT/US2011/036254
§ 371 (c)(1),
(2), (4) Date: Mar. 6, 2012

(87) PCT Pub. No.: WO2012/154186
PCT Pub. Date: Nov. 15, 2012

(65) Prior Publication Data
US 2012/0288911 A1   Nov. 15, 2012

(51) Int. Cl.
*C12M 3/00* (2006.01)
*C12N 11/00* (2006.01)
*B01J 19/18* (2006.01)
*C12M 1/12* (2006.01)
*C12M 1/26* (2006.01)

(52) U.S. Cl.
CPC ............. *C12M 25/16* (2013.01); *C12M 21/08* (2013.01); *C12M 33/00* (2013.01)
USPC .................... 435/286.5; 435/284.1; 422/224; 422/225

(58) Field of Classification Search
CPC ....... C12M 21/08; C12M 25/16; C12M 33/00

USPC .............. 435/286.5, 39, 284.1, 395; 422/119, 422/224, 225; 424/424, 423; 204/403.1–403.15

See application file for complete search history.

(56) References Cited

U.S. PATENT DOCUMENTS 3,572,645 A * 3/1971 Matsuoka ..................... 366/76.7
3,879,245 A * 4/1975 Fetherston et al. ........... 156/245
5,268,224 A * 12/1993 DesMarais et al. ........... 442/370
5,521,079 A    5/1996 Dorian et al.
(Continued)

OTHER PUBLICATIONS

Albrecht, D.R., et al., "Photo- and electropatterning of hydrogel-encapsulated living cell arrays," *The Royal Society of Chemistry*, 2005, vol. 5, pp. 111-118.

(Continued)

*Primary Examiner* — Michael Marcheschi
*Assistant Examiner* — Shanta G Doe
(74) *Attorney, Agent, or Firm* — Foley & Lardner LLP

(57) ABSTRACT

A system for generating a tissue construct includes a mixing chamber, a piston chamber, a reaction chamber, and a pump. The mixing chamber is configured to receive a hydrogel solution and a cell suspension solution. The piston chamber includes a first piston and is configured to receive a mixture of the hydrogel solution and the cell suspension solution from the mixing chamber. The first piston is configured to push the mixture through one or more capillaries into the reaction chamber. The reaction is configured to receive the mixture and a cross-linking initiator. The pump is configured to move the mixture through the reaction chamber such that the mixture and the cross-linking initiator combine to form an encapsulated cell material.

8 Claims, 7 Drawing Sheets

(56) References Cited

U.S. PATENT DOCUMENTS

| | | | | |
|---|---|---|---|---|
| 5,817,381 | A * | 10/1998 | Chen et al. | 428/34.8 |
| 5,882,929 | A * | 3/1999 | Fofonoff et al. | 435/395 |
| 6,773,713 | B2 * | 8/2004 | Bonassar et al. | 424/423 |
| 2003/0068251 | A1 * | 4/2003 | Smith et al. | 422/28 |
| 2009/0162411 | A1 * | 6/2009 | Buensuceso et al. | 424/422 |
| 2010/0213292 | A1 * | 8/2010 | Sullivan | 241/1 |

OTHER PUBLICATIONS

Atala, A., "Engineering tissues, organs and cells," *Journal of Tissue Engineering and Regenerative Medicine*, 2007, vol. 1, No. 2, pp. 83-96.

"European Commission focuses human on tissue engineering potential," Brussels, Jan. 22, 2004, available at http://europa.eu/rapid/pressReleasesAction.do?reference=IP/04/85&format=HTML&aged=0&language=EN&guiLanquage=en, originally printed on Jan. 23, 2012, 2 pp.

Freed, L.E., et al., "Advanced Material Strategies for Tissue Engineering Scaffolds," *Advanced Materials*, Sep. 4, 2009, vol. 21, No. 32-33, 18 pages.

Grayson, W. L.; et al., "Biomimetic approach to tissue engineering," *Seminars in Cell & Developmental Biology*, 2009, vol. 20, No. 6, pp. 665-673.

Hollister, S.J., "Scaffold Design and Manufacturing: From Concept to Clinic," *Advanced Materials*, 2009, vol. 21, No. 32-33, pp. 3330-3342.

International Search Report and Written Opinion received for Intl. Pat. Appln. No. PCT/US2011/036254, mailed Sep. 13, 2011.

Jen, A.C., et al., "Review: Hydrogels for Cell Immobilization," *Biotechnology and Bioengineering*, May 20, 1996, vol. 50, No. 4, pp. 357-364.

Martin, I., "Bioreactor-based roadmap for the translation of tissue engineering strategies into clinical products," *Trends in Biotechnology*, 2009, vol. 27, No. 9, pp. 495-502.

Slaughter, B.V. et al., "Hydrogels in Regenerative Medicine," *Advanced Materials*, 2009, vol. 21, No. 32-33, pp. 3307-3329.

Wendt, D., et al., "Potential and Bottlenecks of Bioreactors in 3D Cell Culture and Tissue Manufacturing," *Advanced Materials*, 2009, vol. 21, No. 32-33, pp. 3352-3367.

International Preliminary Report on Patentability in PCT/US2011/036254 dtd Nov. 21, 2013 (7 pages).

* cited by examiner

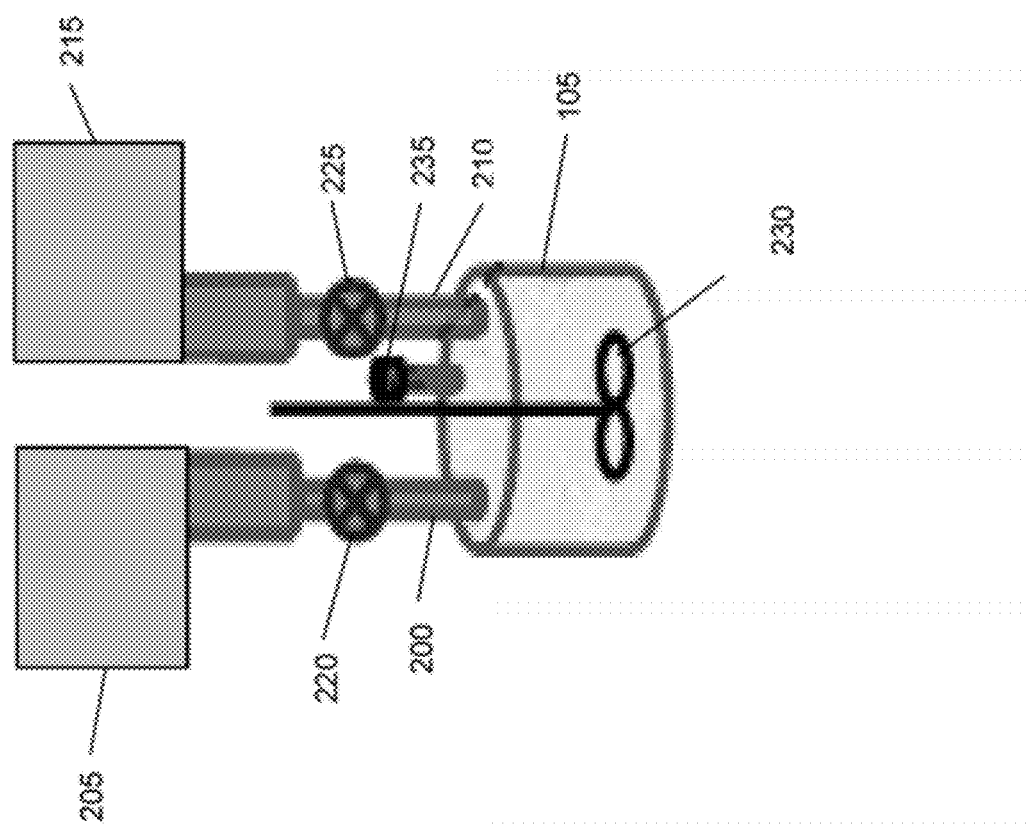

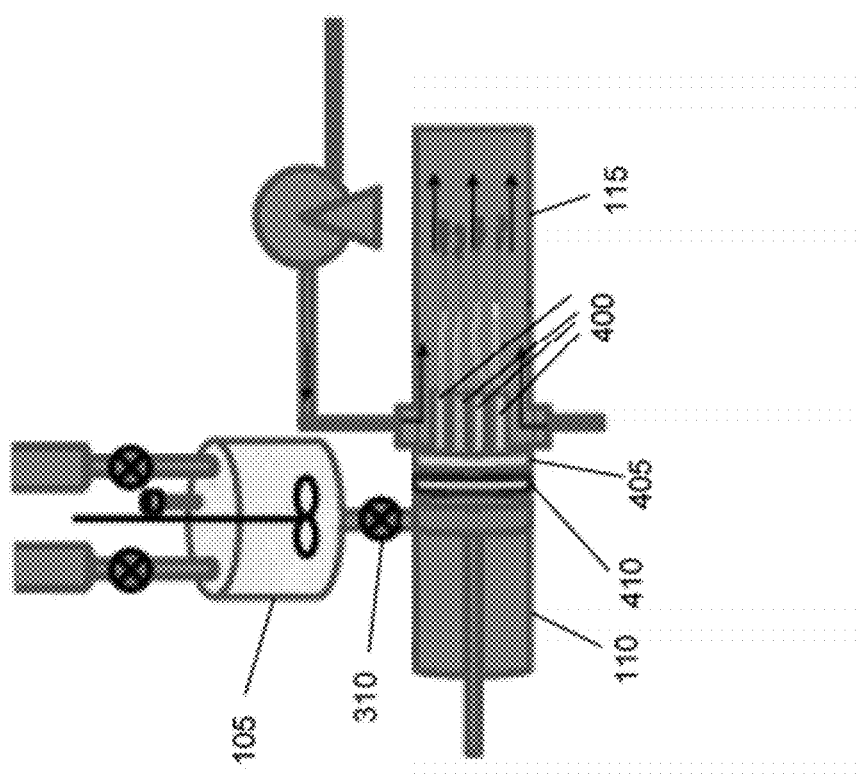

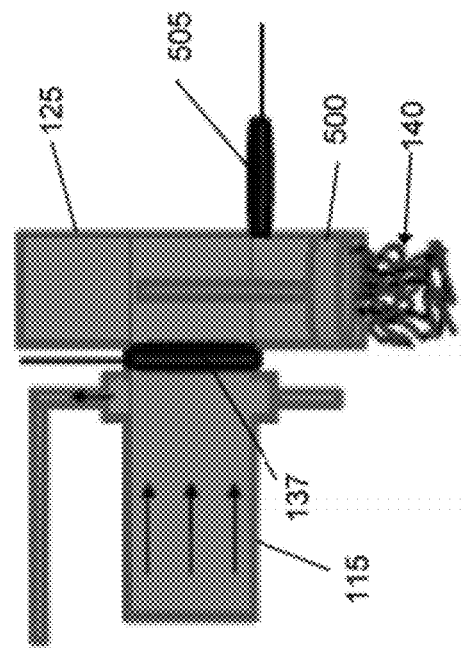
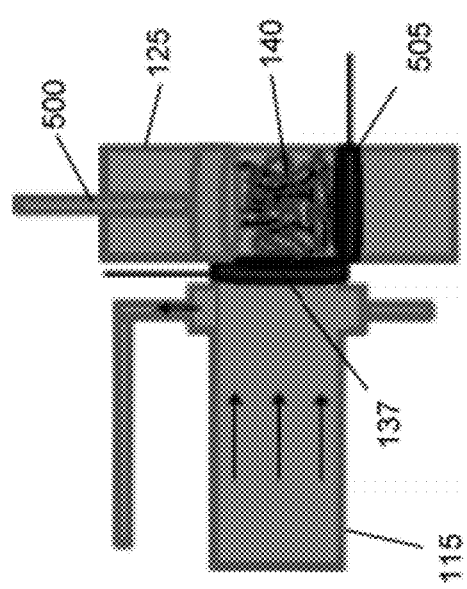
Fig. 5A
Fig. 5B

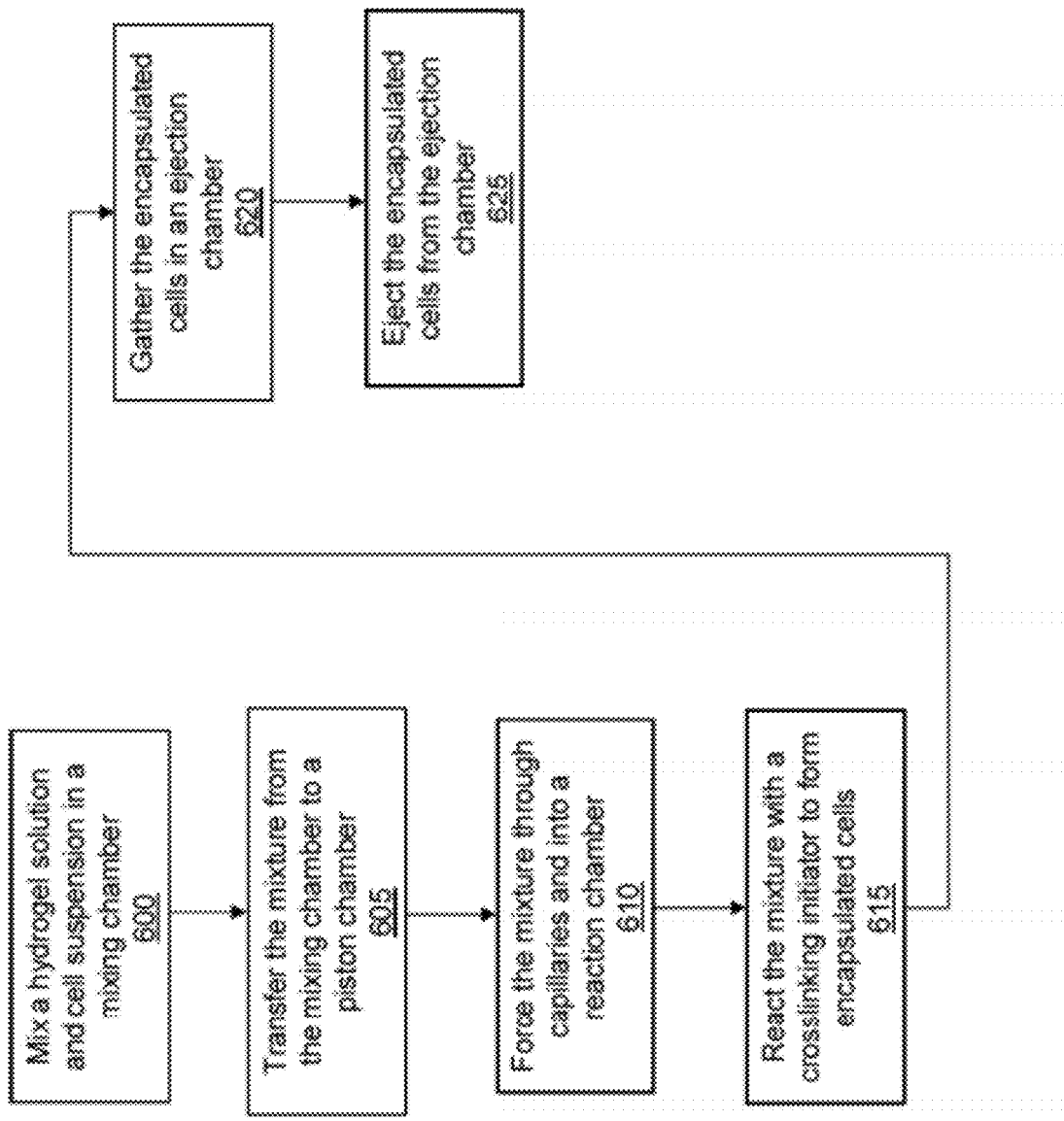

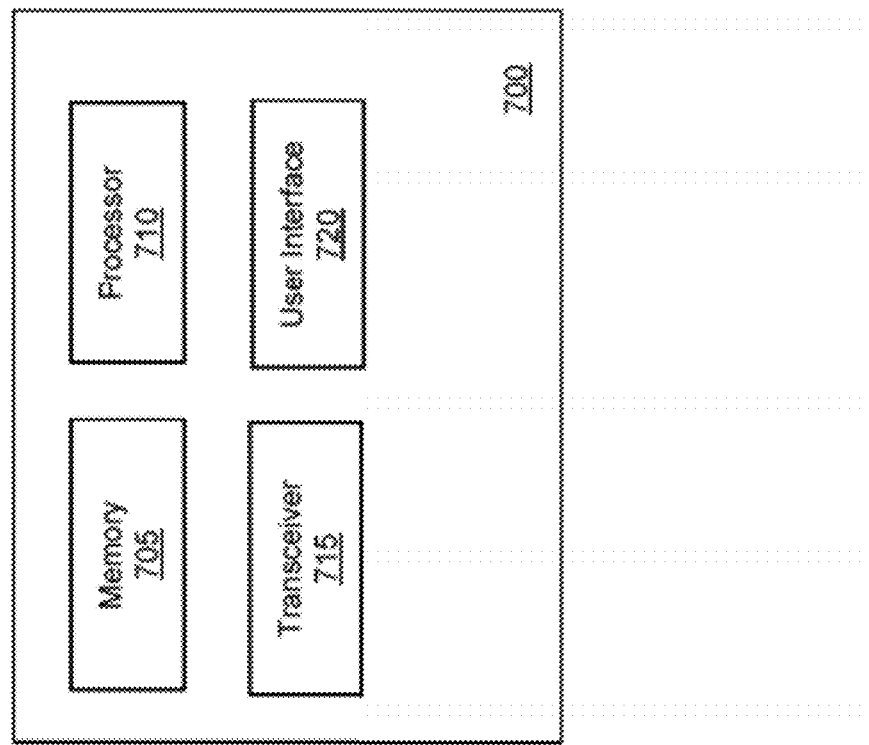

BIOREACTOR FOR ENGINEERED TISSUE

CROSS-REFERENCE TO RELATED APPLICATIONS

This application is a national stage application of International Application Serial No. PCT/US2011/036254, filed on May 12, 2011, the entire disclosure of which is hereby incorporated by reference for all purposes in its entirety as if fully set forth herein.

BACKGROUND

The following description is provided to assist the understanding of the reader. None of the information provided or references cited is admitted to be prior art.

The field of tissue engineering has recently emerged as a strong player in the field of regenerative medicine. Due to their unique properties, hydrogels are ideal candidates for use in tissue engineering applications. Hydrogels are relatively easy to synthesize and they are biocompatible. Hydrogels also allow for the adsorption of biologically active molecules that can influence cellular behavior as well as allow for the mass transport of nutrients and waste. Their similarities with the extra-cellular matrix in structure and sometimes in chemical composition, and their ability to sustain viable and proliferating cells, are desired qualities that hydrogels exhibit for the application of tissue constructs. Their high promise have driven scientists to synthesize structures that are used to mimic tissues that play central roles in our bodies, such as liver tissue, neural tissue, etc.

SUMMARY

An illustrative system for generating a tissue construct includes a mixing chamber, a piston chamber, a reaction chamber, and a pump. The mixing chamber is configured to receive a hydrogel solution and a cell suspension solution. The piston chamber includes a first piston and is configured to receive a mixture of the hydrogel solution and the cell suspension solution from the mixing chamber. The first piston is configured to push the mixture through one or more capillaries into the reaction chamber. The reaction is configured to receive the mixture and a cross-linking initiator. The pump is configured to move the mixture through the reaction chamber such that the mixture and the cross-linking initiator combine to form an encapsulated cell material.

An illustrative process for generating a tissue construct includes mixing a hydrogel solution and a cell suspension solution in a mixing chamber of a tissue generating system. A mixture of the hydrogel solution and the cell suspension solution is drawn from the mixing chamber into a piston chamber. The mixture is pushed through one or more capillaries and into a reaction chamber. The mixture is pumped through the reaction chamber so that the mixture reacts with a cross-linking initiator in the reaction chamber to form an encapsulated cell material.

Another illustrative system for generating a tissue construct includes means for mixing a hydrogel solution and a cell suspension solution in a mixing chamber. The system also includes means for drawing a mixture of the hydrogel solution and the cell suspension solution from the mixing chamber into a piston chamber. The system also includes means for pushing the mixture through one or more capillaries and into a reaction chamber. The system further includes means for pumping the mixture through the reaction chamber so that the mixture reacts with a cross-linking initiator in the reaction chamber to form an encapsulated cell material.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 2 is a diagram of a mixing chamber of a bioreactor in accordance with an illustrative embodiment.

FIG. 4 is a partial view of a bioreactor illustrating the interaction between a piston chamber and a reaction chamber in accordance with an illustrative embodiment.

FIG. 5A is a partial view of a bioreactor illustrating a reaction chamber and an ejection chamber in accordance with an illustrative embodiment.

FIG. 5B is a partial view of a bioreactor illustrating ejection of worm-like hydrogels in accordance with an illustrative embodiment.

FIG. 6 is a flow diagram illustrating operations performed by a bioreactor in accordance with an illustrative embodiment.

FIG. 7 is a block diagram illustrating a computer system 700 for controlling a bioreactor in accordance with an illustrative embodiment.

DETAILED DESCRIPTION

Figure 1:
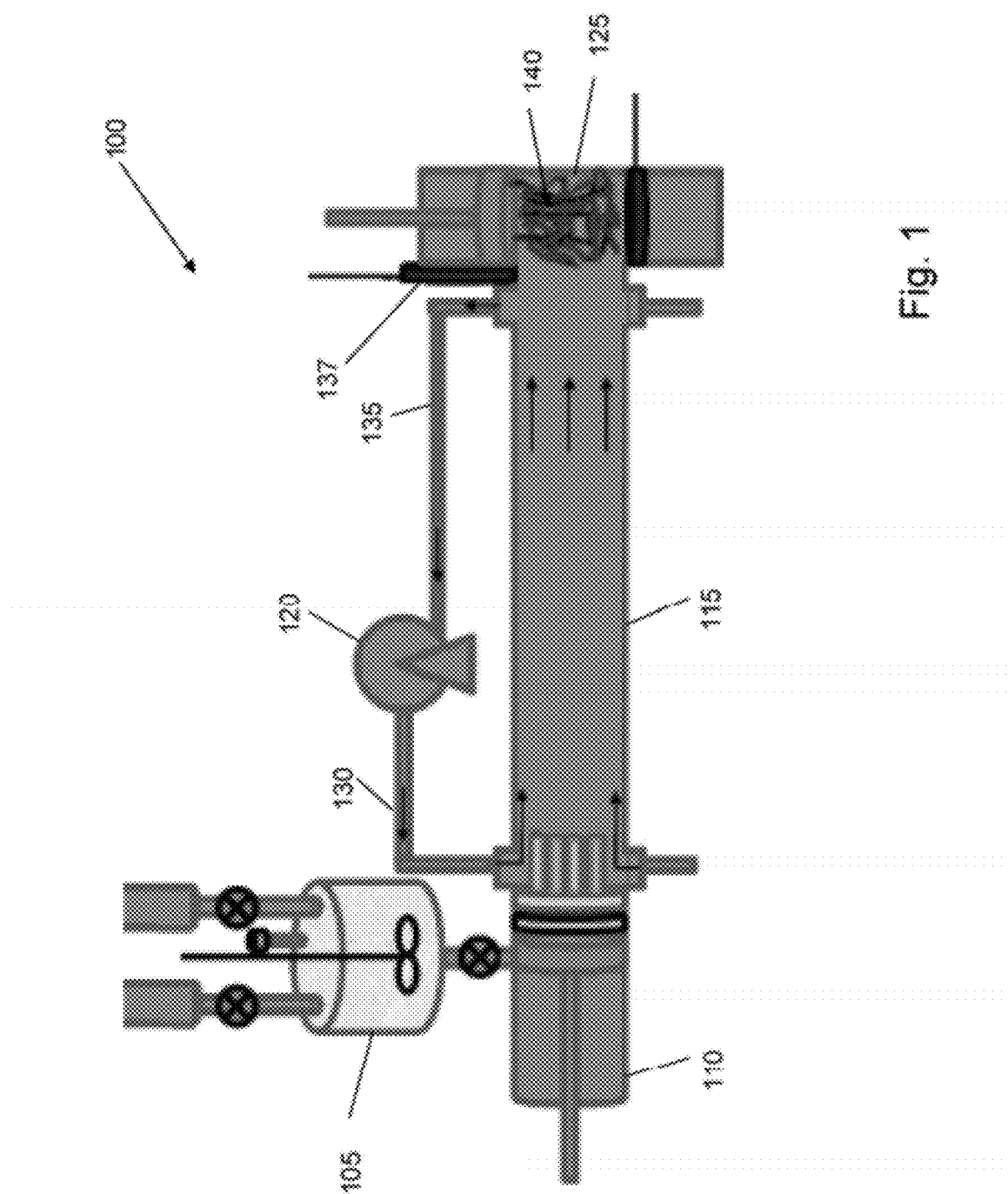
FIG. 1 is a diagram of a bioreactor for manufacturing engineered tissue in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIG. 1 is a diagram of a bioreactor 100 for manufacturing engineered tissue in accordance with an illustrative embodiment. The engineered tissue can be, but is not limited to, bone tissue, cartilage tissue, organ tissue such as liver tissue, pancreatic tissue, or neural tissue, etc. The engineered tissue can be manufactured by bioreactor 100 in the form of tissue scaffolds as known to those of skill in the art. The tissue scaffolds can be used for, but are not limited to, bone reconstruction, cartilage reconstruction, neural tissue regeneration, etc. Bioreactor 100 includes, but is not limited to, a mixing chamber 105, a piston chamber 110, a reaction chamber 115 with a pump 120, and an ejection chamber 125. In an illustrative embodiment, one or more or all of the components of bioreactor 100 can be removable via a threaded connection, friction connection, etc. so that the components can be individually cleaned, sterilized, and/or replaced. One or more or all of the components of bioreactor 100 may also be disposable. A detailed description of each of these components of bioreactor 100 is provided with reference to FIGS. 2-5.

FIG. 2 is a diagram of mixing chamber 105 of bioreactor 100 in accordance with an illustrative embodiment. In one embodiment, mixing chamber 105 can have a volume of between approximately 100 milliliters (mL) and 1 Liter (L) depending on the size of production. Alternatively, the volume mixing chamber 105 may be less than 100 ml or greater than 1 L. In an illustrative embodiment, mixing chamber 105 can be a cylindrical vessel that can be made of a plastic such as but not limited to acrylic (plexi-glass) or a metal such as stainless steel. Both acrylic and stainless steel can be readily sterilized (e.g., plastic can be sterilized in ethylene oxide and stainless steel can be sterilized via heat or ethylene oxide). In some embodiments, the chamber may be designed to be disposable.

In some embodiments, mixing chamber 105 may be connected to a conduit 200 so that mixing chamber 105 is able to receive the contents of a reservoir 205. Mixing chamber 105 can be permanently or detachably mounted to conduit 200, depending on the embodiment. In one embodiment, mixing chamber 105 can be connected to conduit 200 with a screw or other fitting connection. Mixing chamber 105 is also connected to a conduit 210 so that mixing chamber 105 is able to receive the contents of a reservoir 215. Mixing chamber 105, conduit 200, reservoir 205, conduit 210, and reservoir 215 may be made from biocompatible material(s) known to those of skill in the art. In one embodiment, the materials used may be a transparent or opaque rigid plastic such as but not limited to acrylic or Teflon. The materials used may also be metallic such as but not limited to stainless steel, or glass. Conduit 200 includes a valve 220 that is used to control the flow of the contents of reservoir 205 into mixing chamber 105. Conduit 210 similarly includes a valve 225 that is used to control the flow of the contents of reservoir 215 into mixing chamber 105. In an illustrative embodiment, each of valves 220 and 225 can have an open position in which the respective reservoir contents are able to flow into mixing chamber 105, and a closed position in which content flow is prevented. Valves 220 and 225 can be any type of open/close valve(s) known to those of skill in the art. Valves 220 and 225 may be manually controlled by an operator of bioreactor 100 and/or automatically (computer) controlled by a motor or other actuator. In an alternative embodiment, valves 220 and/or 225 may not be included.

In an illustrative embodiment, the contents of reservoir 205 may include a hydrogel solution with uncrosslinked hydrogel materials, and the contents of reservoir 215 may include a cell suspension. Examples of uncrosslinked hydrogel materials may include but are not limited to alginate, polyacrylamide, gels made with hyaluronic acid, polyethylene, etc. In an alternative embodiment, reservoir 205 may include the cell suspension and reservoir 215 may include the hydrogel solution. The cell suspension may include, but is not limited to, neural cells, liver cells, stem cells, cartilage cells, or other types of cells, depending on the type of tissue to be manufactured. The hydrogel solution that is used can be based on the type of cells in the cell suspension. For example, osteoblast cells may be suspended in a PEG-PLA hydrogel or a Peptide amphiphile-Ti composite hydrogel, fibroblast cells may be suspended in a PEG hydrogel, heptocyte cells may be suspended in a HA hydrogel, an alginate hydrogel, or a carboxymethylcellulose hydrogel, etc. Additional examples of cells and corresponding hydrogels can be found in an article titled "Hydrogels in Regenerative Medicine" by Slaughter et al. (from Adv. Mater. 2009, 21, 3307-3329), the entire disclosure of which is hereby incorporated by reference.

Mixing chamber 105 also includes a venting valve 235. Venting valve 235 can be any type of air valve known to those of skill in the art. In an alternative embodiment, venting valve 235 may be a semi-permeable membrane that allows air to be released from mixing chamber 105. In an illustrative embodiment, venting valve 235 does not allow air to flow in to mixing chamber 105. Venting valve 235 is used to release air from mixing chamber 105 that is displaced when the hydrogel solution and/or cell suspension are added to mixing chamber 105. In an illustrative embodiment, venting valve 235 can have an open position in which the displaced air from mixing chamber 105 is released, and a closed position in which air from mixing chamber 105 is unable to escape. In such an embodiment, venting valve 235 can be controlled manually by an operator of bioreactor 100 and/or automatically by a computer controlled motor or other actuator. In an illustrative embodiment, venting valve 235 is placed into the open position as the hydrogel solution and cell suspension are being transferred to mixing chamber 105, and placed into the closed position once the transfer is complete. In an alternative embodiment, venting valve 235 may only have an open position such that displaced air from mixing chamber 105 is always able to be released.

In an illustrative embodiment, valves 220 and 225 are used to place desired amounts of hydrogel solution and cell suspension into mixing chamber 105 from the respective reservoirs. In an illustrative embodiment, approximately 1-10 mL of cell suspension are added to mixing chamber 105 for approximately every 100 mL of hydrogel solution added to mixing chamber 105. In alternative embodiments, different amounts of cell suspension and/or hydrogel solution may be used as known in the art for a particular purpose and/or cell type. In one embodiment, the hydrogel solution and cell suspension are simultaneously added to mixing chamber 105. In the case of non-viscous pre-polymeric solutions, sedimentation of the cells in the cell suspension may occur, preventing the cells from flowing into mixing chamber 105. In such an embodiment, reservoir 215 may not be used and the cell suspension may be directly added to mixing chamber 105 through an aperture in mixing chamber 105. In the case of viscous pre-polymeric solutions, cell sedimentation should not occur and reservoir 215 can be used. In alternative embodiments, the cell suspension may be added before or after the hydrogel solution. The entire contents of reservoirs 205 and 215 can be added to mixing chamber 105. In an alternative embodiment, only a portion of the contents of reservoir 205 and/or reservoir 215 are added to mixing chamber 105. A ratio of hydrogel solution to cell suspension can be controlled by computer software which can determine how long valves 220 and 225 should remain open. In one embodiment, the quantity from each of reservoirs 205 and 215 can be determined by a user and can depend on the type of hydrogel used. For example, a small volume of a highly concentrated cell suspension can be added to the pre-polymeric materials, and the water in the cell suspension can complement the water used in the hydrogel solution. In an illustrative embodiment, reservoir 210, reservoir 215, and mixing chamber 105 can all be mounted to bioreactor 100 with a connection such as but not limited to a screw, with a threaded connection, with a fitted connection, etc. As such, these components can be removed for cleaning, sterilizing, disposal, and/or replacement.

Mixing chamber 105 may include an impeller 230 for mixing the hydrogel solution and the cell suspension within mixing chamber 105. Impeller 230 can refer to one or more blades, one or more magnetic stirrers, or any other object(s) that can be used for mixing. Impeller 230 can be made from a biocompatible material known to those of skill in the art. Impeller 230 can be manually activated by an operator of bioreactor 100 and/or automatically activated by a motor or other actuator. Impeller 230 can be activated before, during, or after the hydrogel solution and cell suspension are added into the mixing chamber. In an alternative embodiment, the mixing can be performed by shaking, rocking, inverting, or otherwise moving mixing chamber 105. In another alternative embodiment, the mixing can be performed by applying external force waves such as ultrasound waves, microwaves, etc. to mixing chamber 105. The amount of time that the mixing occurs may depend on the size of mixing chamber 105, the hydrogel, the temperature, and optionally other factors as known in the art. For smaller mixing chambers that are approximately less than a liter, mixing for one to several minutes may be sufficient. For larger mixing chambers in the range of 1 or more liters, a longer mixing time may be used such as 5 minutes, 10 minutes, 15 minutes, 30 minutes, 60 minutes, etc.

Figure 3B:
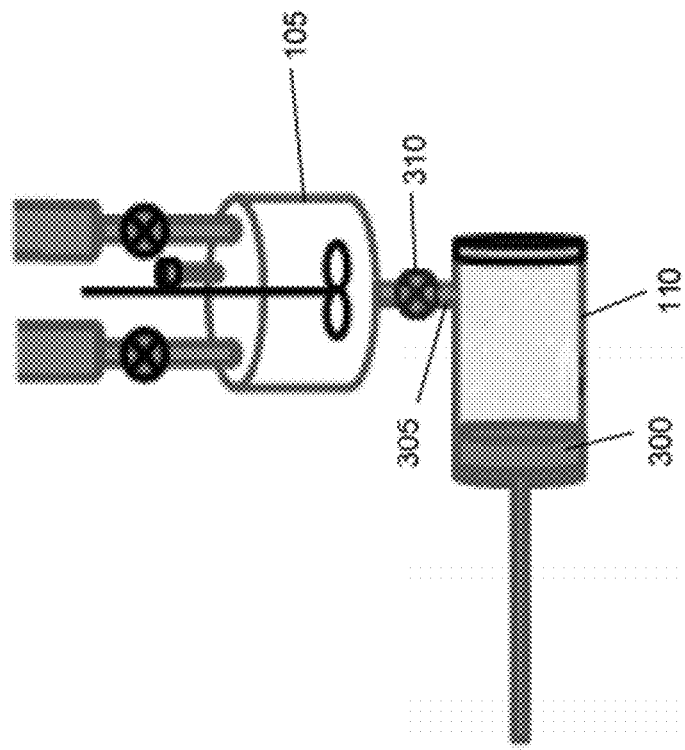
FIG. 3B is a diagram illustrating the piston of the piston chamber in an uncompressed position in accordance with an illustrative embodiment.
Figure 3A:
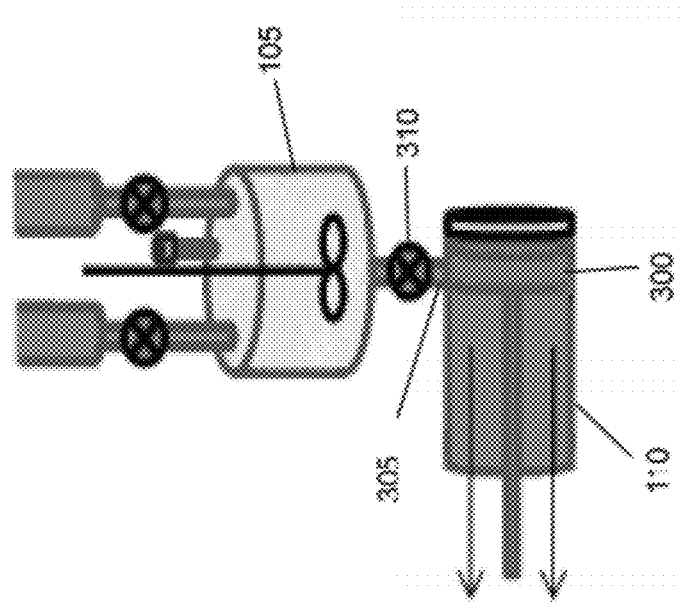
FIG. 3A is a diagram illustrating a piston of a piston chamber in a compressed position in accordance with an illustrative embodiment.

FIG. 3A is a diagram illustrating a piston 300 of piston chamber 110 in a compressed position in accordance with an illustrative embodiment. FIG. 3B is a diagram illustrating piston 300 of piston chamber 110 in an uncompressed position in accordance with an illustrative embodiment. Piston chamber 110 includes piston 300 and a conduit 305 that includes a valve 310. Valve 310 can be any type of valve known to those of skill in the art. Valve 310 has an open position in which the contents of mixing chamber 105 are able to flow into piston chamber 110, and a closed position that blocks the flow of the contents of mixing chamber 105 into piston chamber 110. In an illustrative embodiment, piston chamber 110 can be made of materials such as but not limited to acrylic or stainless steel. In alternative embodiments, other materials may be used. In another illustrative embodiment, piston chamber 110 can have a size and shape similar to that of mixing chamber 105.

After the hydrogel solution and cell suspension are mixed in mixing chamber 105, valve 310 is opened with piston 300 in the compressed position (as illustrated in FIG. 3A). Venting valve 235 illustrated with reference to FIG. 2 may also be in the open position. In an illustrative embodiment, bioreactor 100 may be used in a laminar hood prevent bacteria or other contaminants from entering bioreactor through venting valve 235. In an alternative embodiment, venting valve 235 may include a semi-permeable membrane to let air in and to block out contaminants. In an illustrative embodiment, piston 300 is sized to form an airtight seal with the interior wall of piston chamber 110. As such, moving piston 300 from the compressed position to the uncompressed position creates a suction that draws the mixture from mixing chamber 105 into piston chamber 110. Piston 300 can be moved manually by an operator of bioreactor 100 and/or automatically by a motor or other actuator. In one embodiment, the speed at which the piston moves can depend on the cells utilized to help prevent cell damage. Alternatively, a single piston speed may be used regardless of the cells used. Valve 310 is closed once piston 300 is moved to the uncompressed position as illustrated in FIG. 3B. In an alternative embodiment, piston 300 may initially be in the uncompressed position and the hydrogel/cell mixture may be allowed to flow into piston chamber 110 by gravity.

FIG. 4 is a partial view of bioreactor 100 illustrating the interaction between piston chamber 110 and reaction chamber 115 in accordance with an illustrative embodiment. Reaction chamber 115 includes capillaries 400 through which the mixture from piston chamber 110 passes as it enters reaction chamber 115. Passing the mixture through capillaries 400 subjects the hydrogels to shear forces that help shape the hydrogels into worm-like structures for eventual encapsulation of the cells. The worm-like structures are formed due to the cylindrical shape of capillaries 400. Cell encapsulation is described in more detail below with reference to reaction chamber 115. Capillaries 400 are mounted to an endplate 405 of reaction chamber. In an illustrative embodiment, endplate 405 includes holes or openings to which capillaries 400 are mounted. In an illustrative embodiment, capillaries 400 can have a diameter of between approximately 0.5 millimeters (mm) and 5 mm depending on the desired dimensions of the worm-like structures. In alternative embodiments, the diameter of capillaries may be less than 0.5 mm or larger than 5 mm. In one embodiment, capillaries can have a diameter of approximately 2 mm or less to allow for sufficient mass transport of nutrients.

A valve 410 is used to control access between piston chamber 110 and reaction chamber 115. In some embodiments, valve 410 may be implemented as a movable door that has an open position in which the mixture can flow from piston chamber 110 to reaction chamber 115 and a closed position in which reaction chamber 115 is separated from piston chamber 110 to prevent back flow. In one embodiment, valve 410 can be implemented through the use of a material that allows material to flow into reaction chamber 115 but that prevents back flow into piston chamber 110. For example, valve 410 may be configured as a membrane that separates the piston chamber 110 from the reaction chamber 115, wherein the membrane only allows unidirectional flow from the piston chamber 110 to the reaction chamber 115, so that a new mixture can be introduced into the piston chamber 110 after the mixture is pushed into the reaction chamber 115. Valve 410 may be formed from any biocompatible material such as but not limited to plastic, glass, stainless steel, etc.

In an illustrative embodiment, piston 300 is in the uncompressed position and valve 310 is in the closed position prior to transferring the mixture of hydrogel solution and cell suspension from piston chamber 110 to reaction chamber 115. The mixture can be moved into reaction chamber 115 by opening valve 410 and moving piston 300 into the compressed position as illustrated in FIG. 4. In one embodiment, valve 410 is configured to automatically open as piston 300 begins moving into the compressed position. In an alternative embodiment, valve 410 may be manually controlled and/or computer controlled. As piston 300 is moved from the uncompressed position to the compressed position, the mixture is forced through capillaries 400 and into reaction chamber 115. In one embodiment, partial compression of piston 300 (e.g., an embodiment in which piston 300 is not fully compressed) may be sufficient to force the mixture through capillaries 400. Valve 410 is closed to separate piston chamber 110 from reaction chamber 115 when piston 300 reaches the compressed position and the mixture is transferred.

In an illustrative embodiment, reaction chamber 115 includes a cross-linking initiator solution that is based at least in part on the type of hydrogel used in the hydrogel solution. In an illustrative embodiment, reaction chamber 115 has sufficient volume to hold both the cross-linking initiator solution and the mixture of hydrogel solution and cell suspension. The composition of the cross-linking initiator solution may depend on the chemistry of the hydrogel used. For example, in the case of alginate hydrogels or hydrogels that are cross-linked in the presence of ions, a solution with the appropriate ion can be used as known to those of skill in the art. As an example, if the hydrogel used is an alginate suspension, the cross-linking initiator solution can include $Ca^{2+}$ such that cross-linking occurs between the hydrogel and the cells. In one embodiment in which alginate is used as the hydrogel, a solution with calcium chloride (CaCl) can be used to crosslink the hydrogel by exposing the pre-polymeric materials to the CaCl solution. In an illustrative embodiment, the $Ca^{2+}$ containing solution can be made at different concentrations to adjust the time that it takes for crosslinking to occur (e.g., a higher concentration can decrease the time that it takes for crosslinking to occur) and/or the desired final properties of the hydrogel. In one embodiment, the initial concentration of Ca2+ used can be approximately 50 milli-Moles (mM), however other concentrations such as 10 mM, 25 mM, 60 mM, 80 mM, etc. can be used depending on the embodiment. In the case of hydrogels that involve a chemical initiation, a solution with the chemical initiator at the appropriate concentration can be used as known to those of skill in the art.

Referring again to FIG. 1, reaction chamber 115 includes pump 120 that is connected to an inlet conduit 130 of reaction chamber 115 and to an outlet conduit 135 of reaction chamber 115. Pump 120 circulates the cross-linking initiator solution in reaction chamber 115 and creates a fluid current (or flow) through reaction chamber 115. The fluid flow rate (or current) can depend at least in part on the size of capillaries 400. If each capillary has a diameter of 0.5 mm, the flow rate in each capillary can be approximately 1-2 milliliters/minute (mL/min). This flow rate can be increased by using capillaries with larger diameters, or decreased by using capillaries with smaller diameters. The fluid flow rate can also depend at least in part on the flow rate of pump 120. Pump 120 can be any type of fluid pump known to those of skill in the art. In an illustrative embodiment, due to their mass, the cells and hydrogels are not circulated through outlet conduit 135, pump 120, and inlet conduit 130. In another alternative embodiment, reaction chamber 115 may include one or more additional pumps and corresponding conduits to help circulate the cross-linking initiator and create the fluid flow.

As described above, the hydrogel solution and cell suspension mixture is passed through capillaries 400 so that the hydrogels are formed into worm-like cylindrical structures. The current within reaction chamber 115 helps draw the mixture into reaction chamber 115. The current also helps maintain the hydrogels as worm-like structures as the hydrogels are released from capillaries 400. The cross-linking initiator solution in reaction chamber 115 causes the worm-like hydrogels to encapsulate the cells and form encapsulated cells (or tissue scaffolds) as known to those of skill in the art. The encapsulation is possible due at least in part to the pores inside the hydrogels which partially or fully encapsulate the cells as a result of contact with the cross-linking initiator. The chemical or physical crosslinking in the hydrogel has a pore size distribution. As the crosslinks are initiated, the cells are encaged within these pores inside the polymer. As long as the hydrogel maintains its structure, the cells can be encapsulated within the pores of the gel. In one embodiment, the hydrogel can also be used for chemical signaling. For example, if biologically active chemicals, peptides, or proteins are used to decorate the hydrogel structure, these chemicals can be used to stimulate the cells in many different ways as known to those of skill in the art. In the simplest form, the hydrogel should serve as the platform in which the cells are encaged, supporting them in a three-dimensional structure. In an illustrative embodiment, the hydrogel dimensions also allow for the mass transfer of nutrients to the cells and increases the viability of the cells in the artificial constructs as known to those of skill in the art.

Reaction chamber 115 includes a valve 137 that is used to separate reaction chamber 115 from ejection chamber 125. Valve 137 can be made from any biocompatible material known to those of skill in the art. Depending on the embodiment, valve 137 can be manually controlled and/or automatically controlled by a motor or other actuator. When valve 137 is in an open position (as illustrated in FIG. 1), the fluid flow (or current) within reaction chamber 115 causes the encapsulated cells to accumulate within ejection chamber 125. In some embodiments, outlet conduit 135 may be re-positioned on a side, etc. of reaction chamber 115 to help accumulate the encapsulated cells in ejection chamber 125. FIG. 1 illustrates an accumulation of encapsulated cells 140 within ejection chamber 125. Once the encapsulated cells are accumulated within ejection chamber 125, valve 137 is closed such that ejection chamber 125 is separated from reaction chamber 115.

FIG. 5A is a partial view of bioreactor 100 illustrating reaction chamber 115 and ejection chamber 125 in accordance with an illustrative embodiment. FIG. 5B is a partial view of bioreactor 100 illustrating ejection of encapsulated cells 140 in accordance with an illustrative embodiment. In FIGS. 5A and 5B, valve 137 is in the closed position such that ejection chamber 125 is separated from reaction chamber 115. Ejection chamber 125 includes a piston 500 that is configured to eject encapsulated cells 140 from bioreactor 100. Ejection chamber 125 also includes a valve 505 through which encapsulated cells 140 are ejected. Valve 505 is in the closed position in FIG. 5A, and in the open position in FIG. 5B. In one embodiment, ejection chamber 125 can be detachable from reaction chamber 115 through, in non-limiting examples, a threaded connection, friction fit, etc. so that ejection chamber 125 and encapsulated cells 140 can be removed and transported to another location as appropriate. In another embodiment, ejection chamber 125 and/or piston 500 may not be included. In such an embodiment, encapsulated cells 140 can be removed directly from reaction chamber 115 by scooping, etc.

In an illustrative embodiment, encapsulated cells 140 are accumulated in ejection chamber 125 as described above with reference to FIG. 4. Once encapsulated cells 140 are within ejection chamber 125, valve 137 is placed in the closed position. In one embodiment, a microscopy tool may be used to determine when to close valve 137 and/or when to eject encapsulated cells 140. Any microscopy tool known to those of skill in the art may be used. The microscopy tool can be any type of optical tool that can be used to determine that encapsulated cells 140 have been formed and/or are ready for removal. In one embodiment, the microscopy tool can form part of bioreactor 100. Alternatively, the microscopy tool may be a handheld or other tool that can be used independent of bioreactor 100. In another alternative embodiment, the microscopy tool may not be used. The encapsulated cells 140 are removed from bioreactor 100 by opening valve 505 and activating piston 500 as illustrated in FIG. 5B. The encapsulated cells 140 (or tissue scaffolds) can be used to form tissue as known to those of skill in the art.

In an illustrative embodiment, bioreactor 100 is able to mass produce encapsulated cells in a continuous and efficient manner. For example, as soon as a first mixture is transferred from mixing chamber 105 to piston chamber 110, valve 310 is closed so that mixing chamber 105 can receive additional hydrogel solution and cell suspension to form a second mixture. As soon as the first mixture is pushed into reaction chamber 115 by piston 300, valve 410 is closed, valve 310 is opened, and piston 300 is moved from the compressed position into the uncompressed position to draw the second mixture into piston chamber 110. The first mixture goes through reaction chamber 115 and the encapsulated cells 140 are gathered in ejection chamber 125. Once valve 137 is closed to separate reaction chamber 115 and ejection chamber 125, encapsulated cells 140 formed from the first mixture are ejected and the second mixture is introduced into reaction chamber 115. The process continues with a third mixture, fourth mixture, etc. such that bioreactor 100 is able to generate encapsulated cells in a continuous manner. In some embodiments, one or more portions (or the entire device) are replaced and/or cleaned and sterilized in between batches.

FIG. 6 is a flow diagram illustrating operations performed by a bioreactor in accordance with an illustrative embodiment. In alternative embodiments, fewer, additional, and/or different operations may be performed. In addition, the use of a flow diagram is not meant to be limiting with respect to the order of operations performed. A hydrogel solution and cell suspension are mixed in a mixing chamber in an operation 600. The mixing chamber can be mixing chamber 105 described with reference to FIGS. 1-5. In an illustrative embodiment, the hydrogel solution and the cell suspension are provided to the mixing chamber through respective reservoirs that are in fluid communication with the mixing chamber.

The mixture is transferred from the mixing chamber to a piston chamber in an operation 605. In one embodiment, piston chamber is piston chamber 110 described with reference to FIGS. 1-5. The piston chamber can include a piston that is used to draw the mixture from the mixing chamber into the piston chamber through a valve that separates the two chambers. Once the mixture is drawn into the piston chamber, the valve can be placed into the closed position to separate the mixing chamber from the piston chamber. The mixture is forced through capillaries and into a reaction chamber in an operation 610. In an illustrative embodiment, reaction chamber can be reaction chamber 115 described with reference to FIGS. 1-5. In one embodiment, a valve separates the piston chamber from the reaction chamber. With the valve placed in an open position, the piston within piston chamber can be used to force the mixture through the capillaries and into the reaction chamber. The valve can be placed in a closed position once the mixture is within the reaction chamber. As such, additional mixture can be drawn into the piston chamber.

The mixture is reacted with a crosslinking initiator to form encapsulated cells in an operation 615. In an illustrative embodiment, the reaction occurs within the reaction chamber. The crosslinking initiator can be circulated throughout the reaction chamber using one or more pumps such that a current is formed in the reaction chamber. The encapsulated cells are gathered in an ejection chamber in an operation 620. In an illustrative embodiment, the encapsulated cells are pushed into the ejection chamber at least in part by the current generated in the reaction chamber as a result of the crosslinking initiator flow. The encapsulated cells are ejected from the ejection chamber in an operation 625.

FIG. 7 is a block diagram illustrating a computer system 700 for controlling a bioreactor in accordance with an illustrative embodiment. Computer system 700 can be in wired or wireless communication with the bioreactor, depending on the embodiment. Computer system 700 includes a memory 705, a processor 710, a transceiver 715, and a user interface 720. Memory 705 can be any type of computer memory known to those of skill in the art. In an illustrative embodiment, memory 705 can store computer-readable instructions that, when executed, cause a bioreactor to perform any of the operations described herein. Examples of computer controlled operations can include, but are not limited to, controlling the valves to place desired amounts of the hydrogel solution and/or the cell suspension from their respective reservoirs into the mixing chamber, controlling the venting valve of the mixing chamber, controlling the impeller or other method for mixing the hydrogel solution and the cell suspension in the mixing chamber, control the amount of time that mixing occurs in the mixing chamber, controlling the valve between the mixing chamber and the piston chamber, controlling movement of the piston, controlling operation of the pump and/or flow rate of the pump, controlling movement of the valve that is used to separate the reaction chamber from the ejection chamber, controlling the valve through which encapsulated cells 140 are ejected from the ejection chamber, etc. Processor 710, which can be any type of processor known to those of skill in the art, can be configured to execute the computer-readable instructions stored in memory 705. Transceiver 715 can be used to transmit and receive data from remote sources. In one embodiment, transceiver 715 is configured to receive instructions for controlling the bioreactor from a remote location. User interface 720 allows an operator to interact with and control computer system 700 and/or the bioreactor. User interface 720 can include a keyboard, a display, a mouse, a touch screen, etc.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having"

should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for generating a tissue construct comprising:
    a bioreactor, the bioreactor comprising:
        a mixing chamber configured to receive a hydrogel solution and a cell suspension solution;
        a piston chamber including a first piston, wherein the piston chamber is configured to receive a mixture of the hydrogel solution and the cell suspension solution from the mixing chamber, and wherein the first piston is configured to push the mixture through one or more capillaries into a reaction chamber;
        the reaction chamber configured to receive the mixture and a cross-linking initiator;
        a membrane that separates the piston chamber from the reaction chamber, wherein the membrane only allows unidirectional flow from the piston chamber to the reaction chamber so that a new mixture can be introduced into the piston chamber after the mixture is pushed into the reaction chamber; and
        a pump configured to move the mixture through the reaction chamber such that the mixture and the cross-linking initiator combine to form an encapsulated cell material.

2. The system of claim 1, further comprising a compression chamber configured receive the encapsulated cell material from the reaction chamber, wherein the compression chamber includes a second piston configured to compress the encapsulated cell material into the tissue construct.

3. The system of claim 2, further comprising a microscopy tool for use in determining when to release the tissue construct from the compression chamber.

4. The system of claim 1, wherein the mixing chamber includes an impeller configured to form the mixture by mixing the hydrogel solution and the cell suspension solution.

5. The system of claim 1, wherein the mixing chamber includes a valve that is configured to release air from the mixing chamber as one or more of the hydrogel solution and the cell suspension solution are introduced into the mixing chamber.

6. The system of claim 1, wherein the first piston is drawn through the piston chamber to create a suction that pulls the mixture into the piston chamber from the mixing chamber.

7. The system of claim 6, further comprising a valve that separates the mixing chamber from the piston chamber, wherein the valve is in an open position when the first piston is drawn through the piston chamber to introduce the mixture into the piston chamber.

8. The system of claim 7, wherein the valve is in a closed position when the first piston pushes the mixture through the one or more capillaries into the reaction chamber.

* * * * *

UNITED STATES PATENT AND TRADEMARK OFFICE
CERTIFICATE OF CORRECTION

PATENT NO. : 8,889,403 B2  
APPLICATION NO. : 13/394471  
DATED : November 18, 2014  
INVENTOR(S) : Matos et al.

Page 1 of 1

It is certified that error appears in the above-identified patent and that said Letters Patent is hereby corrected as shown below:

On Title Page 2, item (56), References Cited under "OTHER PUBLICATIONS", in Column 1, Line 7, delete "EN&guiLanquage=en," and insert -- EN&guiLanguage=en, --, therefor.

In the Specification

In Column 1, Line 4, delete "APPLICATIONS" and insert -- APPLICATION --, therefor.

In Column 1, Line 6, delete "a national stage application" and insert -- a U.S. national stage filing under 35 U.S.C. §371 --, therefor.

In Column 4, Line 6, delete "heptocyte" and insert -- hepatocyte --, therefor.

In Column 5, Line 2, delete "reservoir 210," and insert -- reservoir 205, --, therefor.

In Column 6, Line 37, delete "chamber 115" and insert -- chamber 115, --, therefor.

In Column 7, Line 22, delete "Ca2+" and insert -- $Ca^{2+}$ --, therefor.

Signed and Sealed this  
Twelfth Day of May, 2015

Michelle K. Lee  
*Director of the United States Patent and Trademark Office*